United States Patent [19]

Stevens et al.

[11] Patent Number: 4,696,904
[45] Date of Patent: Sep. 29, 1987

[54] APPARATUS AND METHOD FOR THE DETERMINATION OF WATER BY LIQUID CHROMATOGRAPHY

[75] Inventors: Timothy S. Stevens, Midland; Hamish Small, Leland, both of Mich.

[73] Assignee: The Dow Chemical Company, Midland, Mich.

[21] Appl. No.: 843,423

[22] Filed: Mar. 24, 1986

[51] Int. Cl.⁴ .......................................... G01N 33/18
[52] U.S. Cl. ..................................... 436/39; 436/150; 436/161; 422/59; 422/70; 210/635; 210/656; 73/61.1 C
[58] Field of Search .................... 436/39, 161, 150; 422/59, 70; 210/635, 656; 73/61.1 C

[56] References Cited

U.S. PATENT DOCUMENTS

| | | | |
|---|---|---|---|
| 3,913,384 | 10/1975 | Furuya et al. | 73/61 R X |
| 3,935,097 | 1/1976 | Roof | 210/31 |
| 4,265,634 | 5/1981 | Pohl | 73/61.1 C X |
| 4,301,401 | 11/1981 | Roof et al. | 73/61.1 C X |
| 4,343,767 | 8/1982 | Long et al. | 204/409 X |
| 4,404,065 | 9/1983 | Matson | 73/61.1 C X |
| 4,413,505 | 11/1983 | Matson | 73/61.1 C |
| 4,497,199 | 2/1985 | Matson | 73/61.1 C |
| 4,511,659 | 4/1985 | Matson | 73/61.1 C X |
| 4,552,013 | 11/1985 | Matson | 73/61.1 C |

OTHER PUBLICATIONS

Jones et al., "A Study of the Conductivity of Certain Salts in Water, Methyl, Ethyl, and Propyl Alcohols, and in Mixtures of These Solvents," *American Chemical Journal*, vol. XXVIII, No. 5, Nov. 1902, 329-370.
Jones et al., "A Study of the Conductivities of Certain Electrolytes in Water, Methyl, and Ethyl Alcohols, and Mixtures of These Solvents-Relation Between Conductivity and Viscosity," *American Chemical Journal*, vol. XXXII, No. 6, Dec. 1904, 521-583.
Coetzee et al., "Solute-Solvent Interactions," Marcel Dekker, NY and London, 1969, 163-164.
Mitchell & Smith, *Aquametry*, Part I, "A Treatise on Methods for the Determination of Water," 1977, John Wiley & Sons, NY, 2nd ed., pp. 298, 311-317, 320-323.
Mitchell & Smith, *Aquametry*, Part II, "Electrical and Electronic Methods," 1984, John Wiley & Sons, NY, 2nd ed., pp. 1-5, 515-525, 260-263, 266-269.
Mitchell & Smith, *Aquametry*, Part III, "The Karl Fischer Reagent", John Wiley & Sons, NY, 2nd ed., pp. 44-51.
Fehrmann et al., "Uber Die Gel-Chromatographische Bestimmung von Wasser in Kohlenwasserstoffen," *Z. Anal. Chem.*, 1974, 269(2), pp. 116-118.
Bjorkqvist et al., "Sensitive High-Performance Liquid Chromatographic Method for the Determination of Water in Various Samples, *J. of Chrom.*, 1979, 178, pp. 271-276.
Blasius et al., "Austauscher Mit Cyclischen Polyethern Als Ankergruppen-II," Talanta, 1980, 27, pp. 127-141.
DOWEX::*Ion Exchange*, 1964, published by The Dow Chemical Company; no listed author.

*Primary Examiner*—Michael S. Marcus
*Assistant Examiner*—Lynn M. Kummert
*Attorney, Agent, or Firm*—Timothy S. Stevens; Burke M. Halldorson

[57] ABSTRACT

The invention is the novel combination of liquid chromatographic separation of water from other components of an injected sample followed by electrochemical detection and quantitation of the separated water.

11 Claims, 8 Drawing Figures

HPLC DETERMINATION OF WATER WITH NaCl IN THE ELUENT

Eluent:     0.14g NaCl in one liter of methanol at 2mL/min.
Column:     9 x 54 mm AMINEX® 50WX4, Na⁺ ion form, 20-30 micron
Injection:  10 µL loop
Detection:  7.5 µ mho cm$^{-1}$ per 10 mv
Recorder:   10 mv span, normal polarity

MINUTES

HPLC DETERMINATION OF WATER USING MICROPARTICULATE REVERSE PHASE, NORMAL PHASE AND ION-EXCHANGE COLUMNS WITH NaCl IN THE ELUENT

Eluent: 0.14g NaCl in one liter of methanol at 1 mL/min
Column: PARTISIL® 10-ODS-3, ZORBAX®-SIL or PARTISIL® 10-SCX
Injection: 10 μL loop
Detection: 7.5 μ mho cm⁻¹ per 10 mv
Recorder: 10 mv span, reversed polarity

HPLC DETERMINATION OF WATER WITH VARIOUS ACIDS IN THE ELUENT

Eluent: 0.1g paratoluenesulfonic acid (PTSA) in 400mL methanol or 0.02mL 37% HCl in 200mL methanol, or 0.025mL 96% $H_2SO_4$ in 400mL methanol; at 1.5mL/min
Column: 9x21mm, AMINEX® 50WX4, $H^+$ ion form, 20-30 micron
Injection: 50μL loop
Detection: 30μ mho $cm^{-1}$ per 10mv
Recorder: 10mv span, reversed polarity

HPLC DETERMINATION OF WATER
IN A FORMULATION OF DBNPA

Eluent:    0.05 mL 96% $H_2SO_4$ in 800 mL methanol at 1.5 mL/min
Column:    9 x 21 mm, AMINEX® 50WX4, $H^+$ ion form, 20-30 microns
Injection: 1 μL
Detection: 60 μ mho $cm^{-1}$ per 10 mv
Recorder:  8 mv span, reversed polarity

HPLC DETERMINATION OF WATER IN TELONE®-II SOIL FUMIGANT

Eluent: 0.05 mL 96% $H_2SO_4$ in 800 mL methanol at 1.5 mL/min
Column: 9 x 21 mm, AMINEX® 50WX4, $H^+$ ion form, 20-30 micron
Injection: 50 μL loop
Detection: 7.5 μ mho $cm^{-1}$ per 10 mv
Recorder: 10 mv span, reversed polarity 67 ppm $H_2O$ in TELONE-II® soil fumigant $H_2O$

0 — 4
MINUTES

HPLC DETERMINATION OF WATER USING AN ELUENT CONTAINING ACETONITRILE

Eluent: 0.05 mL 96% $H_2SO_4$ in 800 mL acetonitrile at 1 mL/min
Column: 9 x 7 mm, AG® 1x2, $SO_4^{-2}$ ion form, 200-400 mesh
Injection: 100 μL loop
Detection: 15 μ mho $cm^{-1}$ per 10 mv
Recorder: 10 mv span, normal polarity

MINUTES

HPLC DETERMINATION OF WATER IN CARBONTETRACHLORIDE

Eluent: 0.05 mL 96% $H_2SO_4$ in 800 mL methanol at 1.5 mL/min
Column: 9×18 mm AMINEX 50WX4 $H^+$ ion form, 20-30 micron
Injection: 100 μL loop
Detection: Wescan model ICM conductivity detector, range 1, 10 mv output
Recorder: 2mv span, reversed polarity

MINUTES

APPARATUS AND METHOD FOR THE DETERMINATION OF WATER BY LIQUID CHROMATOGRAPHY

FIELD OF THE INVENTION

The invention is in the field of analytical chemistry and is directed towards a method for the determination of water using a liquid chromatography system.

BACKGROUND OF THE INVENTION

Aquametry or the determination of water is an important branch of analytical chemistry. Many analytical systems have been developed to determine water in solids, liquids and gases. Most of these systems are described in 3 volumes of *Aquametry*, Part I, II and III, J. Mitchell, Jr. and D. M. Smith; Wiley - Interscience; 1977, ISBN-0-471-02264-0 (Part I); 1984, ISBN-0-471-02265-9 (Part II); and 1980, ISBN-0-471-02266-7 (Part III).

Most determinations for water are easily made by a Karl Fischer titration. However, interferences are known including oxidizing agents, unsaturated compounds and thio compounds, see *Aquametry*, Part III, supra. Thermal conductivity detection gas chromatography (GC) is probably the second most used method often resulting in a water peak that elutes rapidly, e.g., 1 to 2 minutes, and with good sensitivity, e.g., 1 ppm, see *Aquametry*, Part I, supra. However, with GC the other components of a sample can take much longer to elute than water and can even decompose on-column and interfere with the analysis.

The present inventors were faced with the need to determine water in commercial formulations of dibromonitrilopropionamide (DBNPA), and antimicrobial product of The Dow Chemical Company. DBNPA is an oxidizing agent and reacts with iodide to yield iodine, and thus interferes with the Karl Fischer method. DBNPA is thermally labile and decomposed on-column in a GC. The products of the decomposition (believed to include HBr) corroded and eventually severed the filaments of the GC detector.

The present inventors thus considered high performance liquid chromatography (HPLC). Blasius et al. determined water by HPLC using a cyclic polyether column with a refractive index detector but water and other interfering components eluted without retention, Blasius et al., *Talanta*, 27:127, 1980. Fehrman et al. determined water by size-exclusion chromatography using a refractive index detector. Fehrman et al. used toluene as the eluent (rather than the more commonly used tetrahydrofuran) which significantly improved separation of water from other low molecular weight interfering components, Fehrman et al., *Z. Für Anal. Chem.*, 269(2):116, 1974. However, the DBNPA formulation was not miscible in toluene, and water itself has a limited solubility in toluene. Bjorkquist et al. reacted phenyl isocyanate with water to form N,N'-diphenylurea (NN'DPU), with a total reaction time of about ½ hour, and then analyzed the NN'DPU by reverse phase HPLC, Bjorkquist et al., *J. Chrom.*, 178:271, 1979. The present inventors wanted a simpler and faster procedure than this. Roof et al. used an anion-exchange column with a refractive index, ultraviolet absorption or differential density detector to determine water in a fluorination process stream in about 12 minutes, but with relatively poor column efficiency, i.e., about 30 effective theoretical plates and with poorer sensitivity than the present inventors desired, Roof et al., U.S. Pat. No. 3,935,097.

The determination of water without a prior separation by electrochemical means (for example by electrical conductivity measurement, dielectric constant measurement [dielometry] or oxidation/reduction reactions at electrodes) is extensively discussed in the volume titled *Aquametry* Part II, supra. However, such direct measurements can be seriously inaccurate due to variations in the sample composition unrelated to variations in water concentration. The foregoing patent and literature publications are fully incorporated herein by reference.

It is, accordingly, an objective of this invention to provide a liquid chromatographic system for the determination of water generally applicable but not limited to samples containing oxidizing agents, unsaturated compounds, thio compounds and thermally labile compounds, said system to be relatively rapid and accurate, said system to use an electrochemical detector.

SUMMARY OF THE INVENTION

The invention is the novel combination of liquid chromatographic technology for effectively separating water from other components of a sample and electrochemical detection technology for effectively measuring the separated water.

The invention relates to an apparatus for the determination of water by liquid chromatography comprising an eluent reservoir containing a nonaqueous eluent; said reservoir in fluid communication with a sample injection means; said injection means in fluid communication with a chromatographic separation means; said separation means in fluid communication with a nonreactive electrochemical detector. Nonreactive electrochemical detectors are conductivity detectors and dielometry detectors but not oxidation/reduction detectors.

The invention also relates to a method for the determination of water by liquid chromatography comprising eluting a sample through a separating medium effective to separate water from other components of the sample using a nonaqueous eluent, said method including the further step of effectively electrochemically detecting the separated water of an injected sample in the effluent eluent from said separating medium.

The detector comprises a detector based on the principle of measuring dielectric constant (dielometry), on the principle of measuring electrical conductivity, and on the principle of measuring oxidation/reduction at electrodes.

The invention also comprises the further step of adding an electrolyte to the eluent stream before said stream reaches said detector, said electrolyte being at least partially dissolved before passing through the detector.

The elecrolyte added to the eluent comprises acids such as $H_2SO_4$, HCl and paratoluenesulfonic acid.

The invention alternatively comprises the further step of placing an immobilized electrolyte between the electrodes of the detector, said electrolyte in contact with said effluent. The immobilized electrolyte comprises, for exemplary purposes, gelled electrolyte, liquid ion-exchangers and solid ion-exchangers.

DETAILED DESCRIPTION OF THE DRAWING

Figure 1:
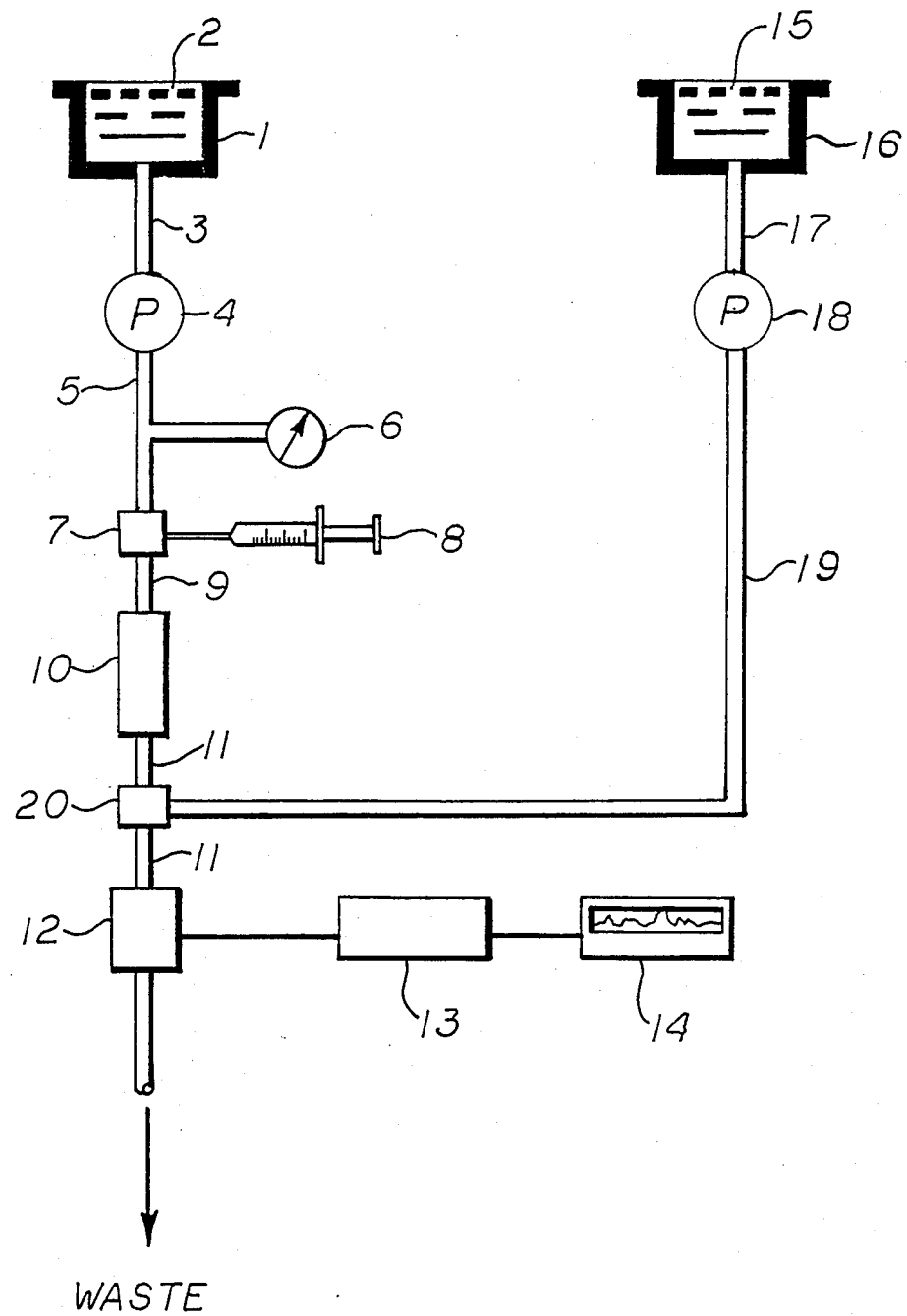
FIG. 1 is a schematic view of a typical apparatus of the invention.

Referring to FIG. 1, there is shown a typical schematic of a liquid chromatographic system which is desirably used in practicing the invention, which comprises an eluent reservoir 1 containing eluent 2 which is directed to pump 4 by tubing 3 and then to sample injection valve 7 by tubing 5. A pressure gauge 6 allows the monitoring of the eluent pressure in tubing 5. Sample is loaded into sample injection valve 7 using syringe 8. Tubing 9 directs eluent to column 10. The effluent from column 10 is directed through tubing 11 to flow-through detector cell 12 and then to waste. Recorder 14 visualizes the detection of the separated water peak in cell 12 by means of detector electronics 13.

Optionally, reagent 15 comprising an electrolyte dissolved in a nonaqueous solvent, contained in reagent reservoir 16, is directed to pump 18 by tubing 17 and then to mixing tee 20 by tubing 19.

DETAILED DESCRIPTION OF THE INVENTION

Ion-exchange resins have a known affinity for water, see for example *DOWEX:: Ion Exchange,* published by The Dow Chemical Company, 1964, specifically page 33, and Roof, supra. A preferred separating medium is a chromatographic column of sulfonated styrene-divinylbenzene copolymer/acid-type ion-exchange resin such as Bio-Rad Laboratories (P.O. Box 4031, Richmond, Calif. 94804) Aminex ® 50WX4, 20 to 30 micron size, catalog nuber 147-4203, packed in a Cheminert ® Model L9-9-MA-13 column available from The Anspec Company, P.O. Box 7730, Ann Arbor, Mich. 48107, catalog number H7224.

Also preferred are other ion-exchange mediums such as quaternized styrene-divinylbenzene copolymer base-type ion-exchange resins such as Bio-Rad Laboratories, supra, AG ® 1×2, 200 to 400 mesh size, catalog number 745-1251. Also useful in the invention are silica based ion-exchange columns such as Whatman Corporation's Partisil ® SAX anion exchange column or Partisil SCX cation exchange column, available from The Anspec Company, supra, catalog number H6303 and H6311, respectively.

Size-exclusion columns have a known ability to separate water in HPLC, for example, see Fehrman et al., supra. Size-exclusion columns having effective pore sizes such as the silica based Brownlee Aquapore ® OH-100 column or the TSK Sphereogel 2000 SW column available from The Anspec Company, supra, catalog numbers H1474 and H4548, respectively are believed useful in the invention.

Size-exclusion columns using porous polymer separation media, such as Waters Associates μ-Styragel ®, are also believed to be useful in the invention. However, as with the sulfonated or quaternized styrene divinylbenzene acid- or base-type ion-exchange resins, which swell varyingly depending on the specific eluent, many porous polymer size-exclusion media must be equilibrated with the eluent before packing the chromatographic column.

The separating media believed to be effective for the invention comprise a packed-type chromatographic column and a capillary-type chromatographic column.

Silica based normal phase columns such as the Du Pont Zorbax ® SIL column are useful in the invention and are believed to work as size-exclusion columns.

Silica based reverse phase columns such as Whatman Partisil ODS-1 and ODS-3 columns are useful in the invention and are also believed to work as size-exclusion columns.

The essential feature of the separating medium of the invention is that it effectively chromatographically separates the water of an injected sample from other components of the sample using a nonaqueous eluent. Specifically, if the electrochemical determination of water is not seriously interfered with by the other components of the sample, then there is little compulsion to use this invention. However, when one or more of the other components of a sample do interfere, then separating them from the water of the sample and presenting this water to the detector in the matrix of the eluent can be an effective means to eliminate serious interferences with detection and analysis. Therefore, the specific chromatographic column used is not critical as long as it performs the above-mentioned effective separation function in an otherwise operable system.

A preferred eluent comprises methanol or acetonitrile. Eluents believed to be effective in the invention comprise ethanol, propanol ethylene glycol, benzene, toluene, carbon tetrachloride, chloroform, cyclohexane, heptane, tetrahydrofuran and toluene. The specific eluent used is not critical as long as it effectively interacts with the chromatographic media to separate water from other components of the sample and as long as the detector used will function to effectively detect the separated water in the eluent in an otherwise operable system.

Ideally, the concentration of water in the eluent is zero. However, some water can be tolerated. Preferably, the concentration of water in the eluent is no more than 100 times the concentration of water in the sample and more preferably the concentration of water in the eluent is no more than 10 times the concentration of water in the sample e.g., for a sample containing 30 ppm of water, the eluent preferably will contain less than about 300 ppm of water. Most preferably, the concentration of water in the eluent is less than the concentration of water in the sample e.g., for a sample containing 5000 ppm (0.5 percent) of water, the eluent most preferably will contain less than about 5000 ppm of water.

Optimally, the eluent should not react with the other components of the sample to produce significantly interfering amounts of water. For example, ketones and aldehydes can react with methanol to form ketals and acetals with the production of water as a by-product. Some organic acids will react with methanol to form esters with the production of water as a by-product. These interferences are well known with the Karl Fischer method for the determination of water and are eliminated by replacing the methanol in the Karl Fischer reagent with another non-reactive solvent. In this invention the same can be done, for example by using an acetonitrile based eluent instead of a methanol based one.

The sample should be preferably miscible in the eluent. Thus, for many samples methanol or acetonitrile based eluents are preferred due to the excellent ability of these solvents to form homogeneous solutions with other solvents and components. However, it is not critical that the sample dissolve in the eluent. For example, the invention is used to determine water in clay based agricultural formulations by first shaking said formulation with HPLC grade methanol to extract water in the formulation and then injecting the methanol extract after said extract is filtered to remove the clay. It is also believed to be possible to determine water in a gas sample by, for example, contacting the gas with a liquid that would extract the water and then injecting said liquid.

A highly preferred detector of the invention is an electrical conductivity detector such as the Wescan Model ICM (Wescan Instrument Inc., 3018 Scott Blvd., Santa Clara, Calif. 95050).

The test of effective electrochemical detection of the separated water of the injected sample in the effluent from the separating medium comprises the well-known signal-to-noise ratio, where the signal relates to the detectors' response to said water and the noise relates to the variation in response seen at the baseline of the chromatogram. The signal-to-noise ratio must be greater than 2 for effective detection. The signal-to-noise ratio can be improved, as is well known in the art, by employing active or passive filters in the electronic circuits of HPLC systems. The signal-to-noise ratio can also be improved (made larger) by injecting a larger volume of sample or by employing a more efficient column in an otherwise operable system. However, all of these techniques are limited in their beneficial effects and thus the detection limit of the invention is also limited. On the other hand, samples containing relatively high concentrations of water, e.g., 20 percent water, may require system modifications to prevent overloading such as using a smaller injection volume.

The sensitivity of detection of water using an electrical conductivity detector is significantly increased when an electrolyte is present in the eluent. The conductivity detector responds to the electrolyte and the difference in response, between a matrix of eluent and a matrix of eluent and the separated water, is greater when an electrolyte is present in the eluent. This is an example not of direct but rather indirect measurement of water concentration. A highly preferred electrolyte is an acid such as, but not limited to, $H_2SO_4$, HCl or paratoluenesulfonic acid. However, samples containing hydroxide ion, for example, will react with acid to form water. Also preferred as an electrolyte to be present in the eluent is a salt such as, but not limited to, NaCl, KCl or LiBr. The sensitivity of detection of water using the preferred conductivity detector is not as good with said salt as with said acid, but the use of said salt does eliminate the interference from hydroxide ion and is one means of avoiding said interference in the event said interference is significant.

An electrolyte believed useful in the invention when using a conductivity detector is a base such as sodium hydroxide or tetrabutylammonium hydroxide. The specific electrolyte used, whether acid, base or salt, organic or inorganic or a mixture thereof is not critical. Optimally, the electrolyte used does not result in significantly interfering reactions with sample components and does not significantly degrade the eluent. It is believed that the most preferred acid and base electrolytes are strong acids and bases, that is acids with $pKa_1$ values less than 1 and bases with $pKb_1$ values less than 1. However, $H_3PO_4$ with a published $pKa_1$ value of 2.12 is quite useful and to a lesser extent even acetic acid with a published $pKa_1$ value of 4.73. The concentration of electrolyte added to the eluent is optimized by testing for optimum signal-to-noise ratio, supra, for a given system. However, it can be desirable to have a relatively high electrolyte concentration in the eluent when using an ion-exchange column, if the sample contains one or more electrolytes, to maintain the ion form of the column.

Where the optionally employed electrolyte is added to the eluent is not critical as long as the addition step occurs before the eluent passes to the detector and as long as the electrolyte is at least partially dissolved in the eluent. For example, it should also be possible to add the electrolyte to the eluent after it emerges from the chromatographic media and before the eluent flows to the detector.

Postcolumn reagent addition is well known to the art of HPLC. One advantage contemplated in this invention with the use of postcolumn electrolyte addition is the potential elimination of interferences. For example, when a sample contains hydroxide ion and the eluent contains an acid, the acid reacts with the hydroxide ion upon injection producing water, said water then a potential interference. On the other hand, if the chromatographic media separates water from hydroxide ion and the acid is added to the eluent following the chromatographic media, then two water peaks will be seen by the detector. One water peak will result from the water originally in the sample at the standard retention time of water. The other water peak from the water produced by the reaction of acid with hydroxide will be at a different nonstandard retention time and will not interfere.

Any solvent used as a carrier with postcolumn electrolyte addition ideally has a water concentration of zero. However, some water can be tolerated. Preferably, the concentration of water in a postcolumn addition electrolyte solvent is no more than 100 times the concentration of water in the sample and more preferably no more than 10 times the concentration of water in the sample. Most preferably, the concentration of water in a postcolumn addition electrolyte solvent is less than the concentration of water in the sample.

Examples of other detectors believed to be useful in the invention comprise those measuring dielectric constant and those incorporating oxidation/reduction reactions at electrodes.

It is believed to be preferred to add an electrolyte to the eluent before the eluent reaches the detector when the detector is an oxidation/reduction detector since such detectors generally require a supporting electrolyte as is well known in the art. However, said detectors do not always require a supporting electrolyte. It is also believed to be preferred to add an electrolyte to the eluent before the eluent reaches the detector when the detector is a dielometry detector in this invention since the dielectric constant of a solvent can be significantly altered when it contains an added electrolyte as is well known in the art.

Alternatively, the electrolyte can be added to the eluent between the sample injection means and the chromatographic separation means or at any other point before the eluent reaches the detector. A highly preferred embodiment of the invention is to mix the electrolyte with the eluent in the eluent reservoir 1 of FIG. 1.

The electrolyte need not be mixed with a carrier solvent and pumped into the eluent but can also diffuse into the eluent across a membrane. In other words, how the electrolyte gets into the eluent before the eluent reaches the detector is not critical to the invention.

When an immobilized electrolyte is effectively employed within the detector, it should be placed between the electrodes of the detector and said electrolyte should contact said effluent. When thus employed, it is believed that water, separated from other components of the sample and entering the detector, can interact with said immobilized electrolyte to enhance the detector's direct or indirect response to said water. The above reference to placing the immobilized electrolyte between the electrodes should not be construed to mean directly and exactly between them as it may be preferable to effectively dispose the immobilized electrolyte away from a point equidistant from the electrodes but still within or adjacent the space measured by the electrodes. The immobilized electrolyte can contact one or more of the electrodes.

The following examples further illustrate the various aspects of the invention.

EXAMPLE 1

An HPLC system generally similar to FIG. 1 (except that no postcolumn reagent addition system 15 to 20 is used) is assembled including an LDC Constametric ® III pump, a Rheodyne ® 7120 sample injection valve, a 9 × 54 mm column of Bio-Rad Aminex 50WX4 ion-exchange resin, in the $Na^+$ ion form packed in a Cheminert LC-9-MA-13 column, a Chromatronix ® CMA-1 conductivity meter with associated MCC-75 flow-through cell and a Sargent ® SRG-1 strip chart recorder. The eluent is composed of HPLC grade methanol containing 0.14 g of NaCl per liter. The pump is set to deliver 2 ml of eluent per minute. The injection valve is fixed with a predetermined loop size to deliver about 10 μl of sample. The detector is set to a sensitivity of 7.5 micro mho per cm for a 10 mv output. The recorder is set at a full scale response of 10 mv.

Figure 2:
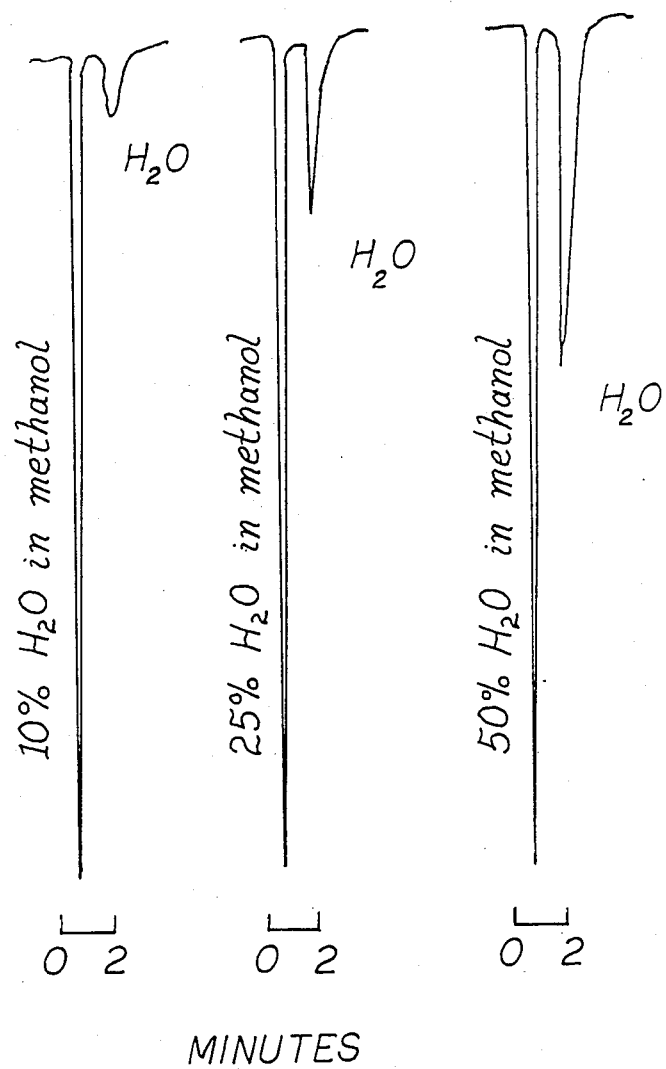
FIGS. 2 through 8 are chromatograms showing the determination of water using the invention and are associated with Examples 1 through 10 below.

Three successive injections of standards of known amounts of water in methanol is then made and the chromatograms shown in FIG. 2 result.

In FIG. 2, two dips ("peaks") are seen in the chromatogram for each injection. The one at about 0.8 minutes is explained as the void volume upset. The one at about 2.1 minutes is explained as the water "peak" and its size is generally proportional to the amount of water in the injected standard. Doubling the amount of NaCl in the eluent doubles the water "peak" height and also doubles the background conductivity of the eluent from about 250 micro mho per cm to about 500 micro mho per cm. As expected, the baseline noise increases with increased background conductivity, and the limit of detection observed with either eluent is about 0.1 percent water (in a standard) with a 500 μl injection. Using LiBr in the eluent instead of NaCl results in similar system performance. Reversing the recorder polarity results in upscale "peaks" and this becomes standard operating procedure for this mode of the invention.

EXAMPLE 2

Figure 3:
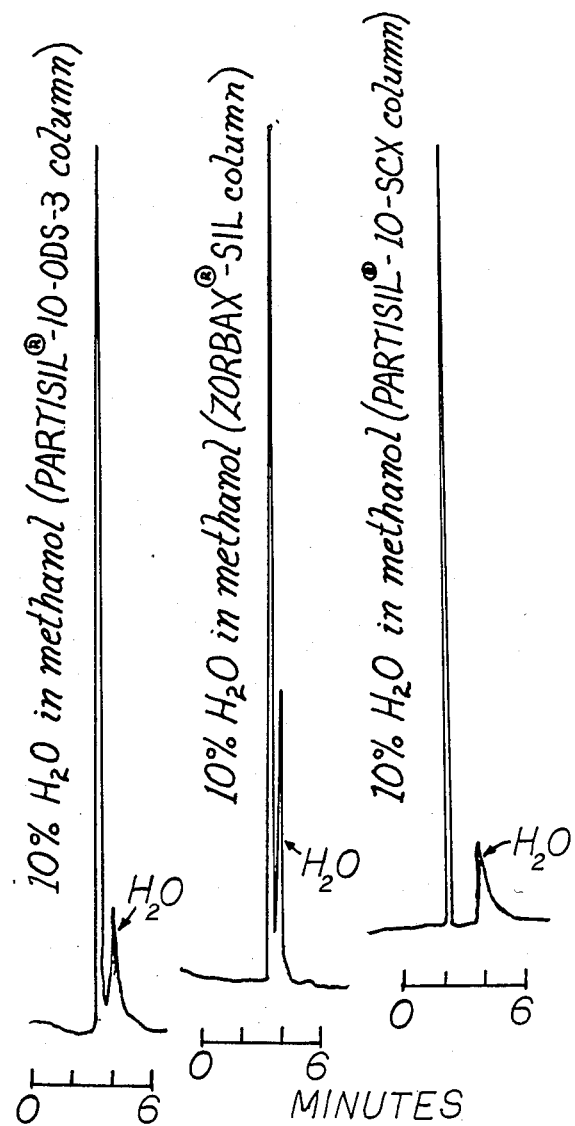

The system of Example 1 is exactly reproduced except that the column used in Example 1 is replaced with a Whatman Partisil 10-ODS-3 column, or a Du Pont Zorbax SIL column, or a Whatman Partisil SCX column and the eluent flow rate is changed to 1 ml per minute. FIG. 3 shows chromatograms resulting from the injection of a standard containing 10 percent water in methanol for each column.

With the use of each column of FIG. 3, a retained water peak resulted whose height is generally proportional to the amount of water injected. This example demonstrates the wide range of column types useful in the invention.

EXAMPLE 3

Figure 4:
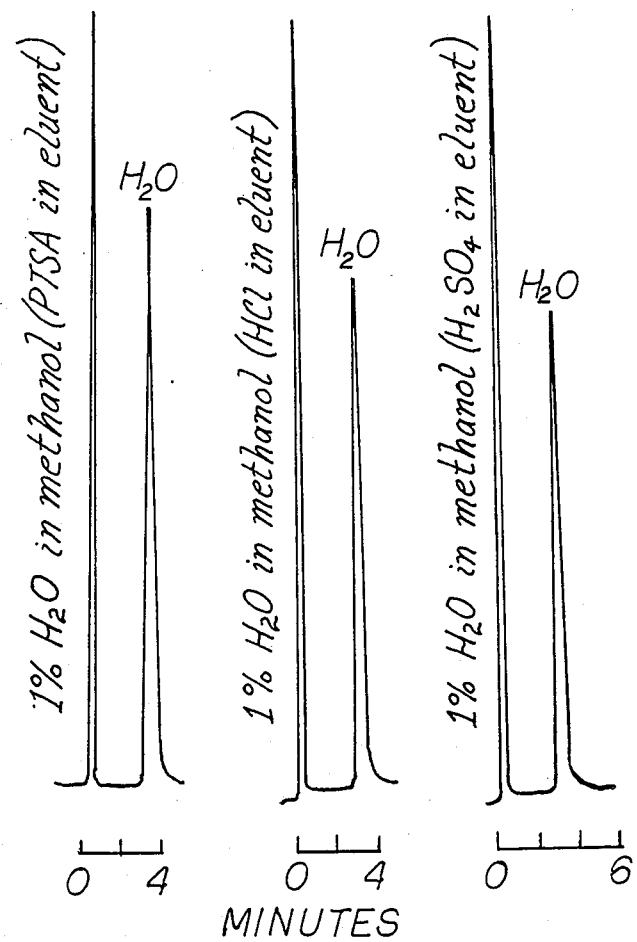

The system of Example 1 is exactly reproduced except that the column is shortened to 9×21 mm and the NaCl in the eluent is replaced with paratoluenesulfonic acid (PTSA), HCl or $H_2SO_4$ and the flow rate of the eluent is changed to 1.5 ml per minute as described in detail in FIG. 4.

As shown in FIG. 4, the use of HCl, $H_2SO_4$ or PTSA in an eluent of methanol using a 9×21 mm column of $H^+$ ion form Aminex 50WX4 results in improved detection sensitivity. Using the NaCl containing eluent of FIG. 2, a 50 μl injection of 1 percent $H_2O$ in methanol results in a water peak 0.11 micro mho per cm tall. Using any of the above acids (also of a concentration sufficient to give an eluent background conductivity of about 250 micro mho per cm) results in a water peak about 18 micro mho per cm tall (see FIG. 4), an increase in sensitivity of about 160 fold. This example demonstrates the improvement in sensitivity observed with the addition of acid to the eluent versus the addition of a salt to the eluent when using a conductivity detector.

EXAMPLE 4

The system of Example 3 is exactly reproduced except that the eluent was 0.05 ml of 96 percent $H_2SO_4$ mixed with 800 ml of HPLC grade methanol, the injection valve is changed to inject about 1 μl of sample, the detector sensitivity is changed to 60 micro mho per cm per 10 mv output and the recorder sensitivity is changed to 8 mv full scale response. When an injection of 20 percent dibromonitrilopionamide (DBNPA) in a water/glycol based formulation is made, the chromatogram shown in FIG. 5 results.

Figure 5:
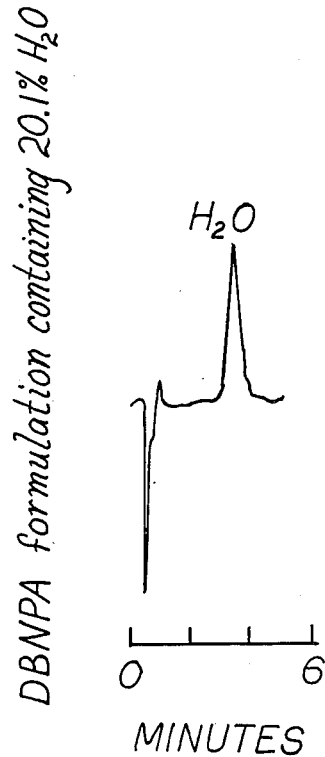

Based on the water peak size for injections of known standards of water in methanol (not shown) the concentration of water in the DBNPA sample of FIG. 5 is estimated to be 20.1 percent (20.1 g $H_2O$ per 100 ml of sample). When the sample is injected 10 times, a statistical evaluation of the data indicates a standard deviation of the water concentration of 0.22 percent. This example demonstrates the utility of the invention for a sample that interferes with the Karl Fischer method and with the gas chromatographic method for the determination of water.

EXAMPLE 5

The system of Example 4 is exactly reproduced except that the sample injection volume is changed to about 50 μl, the detector sensitivity is changed to 7.5 micro mho per cm per 10 mv output and the recorder span is changed to 10 mv. When an injection of Telone ® II soil fumigant (mixed isomers of dichloropropenes, a product of The Dow Chemical Company) is made, the chromatogram shown in FIG. 6 results.

Figure 6:
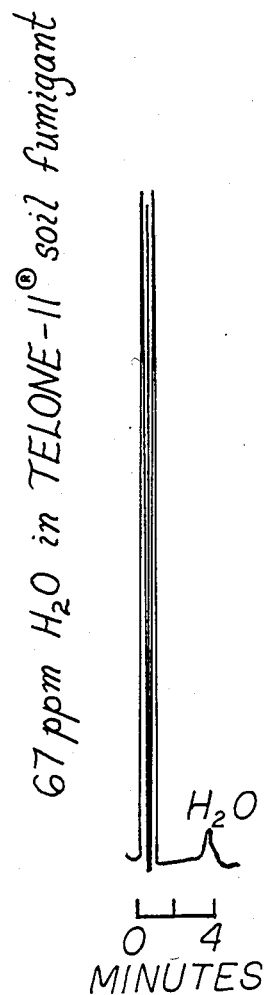

Based on the water peak size for injections of known standards of water in methanol (not shown) the concentration of water in the Telone II sample of FIG. 6 is estimated to be 67 parts per million (ppm) (67 mg of water per liter of sample). A GC analysis of the same sample estimates a water level of 71 ppm. In the GC analysis, the water elutes at about 2 minutes followed by dichloropropene peaks for the next 45 minutes. Thus, the HPLC procedure is faster overall. Trace levels of water can not be determined in Telone II soil fumigant by the Karl Fischer method since iodine adds across the double bonds of the dichloropropenes.

As a rule, water elutes as the last peak in the chromatogram with this embodiment of the invention, well resolved from the other components of a sample. However, dimethylsulfoxide (DMSO) elutes just before water and interferes. Nevertheless, it is clear that the invention can be used to determine DMSO and perhaps other compounds in addition to water. A compound that responds similarly as water responds and is effectively separated from water is contemplated as a candidate as an internal standard with the invention.

EXAMPLE 6

The system of Example 5 is exactly reproduced except that the eluent is changed to 0.05 ml of 96 percent $H_2SO_4$ in 800 ml of acetonitrile (at a flow rate of 1 ml per minute), the column is changed to a 9×7 mm one packed with Bio-Rad AG 1×2, $SO_4^{-2}$ ion form, 200 to 400 mesh, ion-exchange resin, the injection volume is changed to about 100 μl, the detector sensitivity is changed to 15 micro mho per cm per 10 mv output and the recorder polarity is reversed. When an injection of 0.5 percent water in acetonitrile is made, the chromatogram shown in FIG. 7 results.

Figure 7:
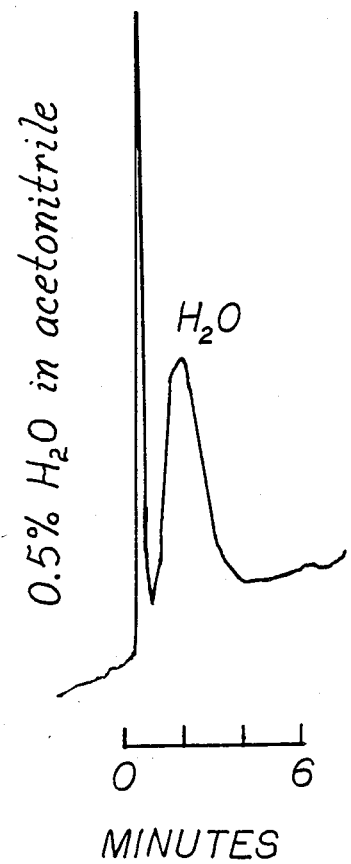

The water peak in FIG. 7 is positive not negative. In addition, the baseline conductivity in FIG. 7 is about 36 times lower than in FIG. 6 while the response for the same amount of water injected with the system of FIG. 6 or 7 (in units of micro mho per cm×ml of the water peak width at half height) is about the same. Therefore, the use of a more efficient chromatographic column with this embodiment of the invention is expected to result in potentially increased detection sensitivity over the embodiment of FIG. 6. One such column contemplated is a size-exclusion column of selected exclusion characteristics specifically designed for separation of relatively low molecular weight components such as water. Another such column contemplated is an ion-exchange column packed with partially sulfonated or partially aminated styrene-divinylbenzene copolymer beads.

EXAMPLE 7

Figure 8:
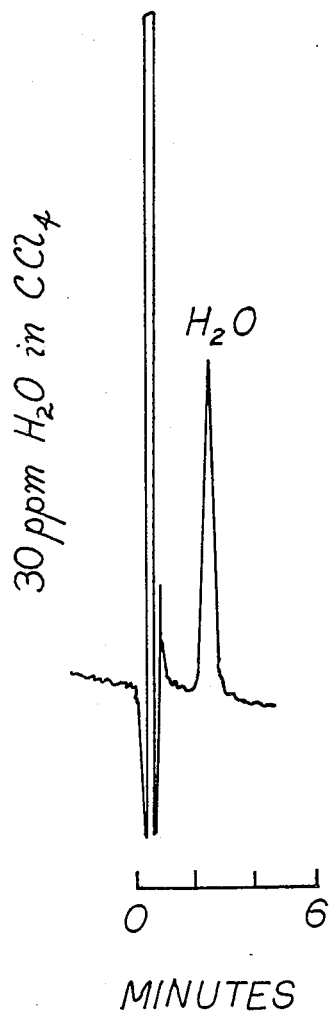

The system of Example 5 is exactly reproduced except that the column length is changed to 18 mm, the injection volume is changed to about 100 μl, the recorder sensitivity is changed to 2 mv full scale and the conductivity detector is changed to a Wescan Model ICM, set at range 1 and for 10 mv output. The concentration of water in the eluent is about 100 ppm. When an injection of carbontetrachloride containing 30 ppm of water is made the chromatogram of FIG. 8 results.

This example demonstrates the high sensitivity of this highly preferred embodiment of the invention.

EXAMPLE 8

The system of Example 4 is exactly reproduced except that a KRATOS Post Column Reagent Addition Device, Model PCR-1 is added (as generally shown by elements 15 to 20 of FIG. 1), the eluent is HPLC grade methanol containing no added $H_2SO_4$ at a flow rate of about 1.5 ml per minute. The post column reagent is 0.1 Ml of 96 percent $H_2SO_4$ dissolved in 800 ml of HPLC grade methanol. The post column reagent flow rate is about 1.5 ml per minute. When an injection of DBNPA in a water/glycol based formulation is made (same sample as Example 4) a chromatogram generally similar to FIG. 5 is believed to result except that the peak height is believed to be about one-half of that in FIG. 5.

EXAMPLE 9

The system of Example 1 is exactly reproduced except that the eluent is composed of HPLC grade methanol containing 0.14 g of sodium hydroxide per liter. When an injection of a sample containing water is made, a water response is believed to result that is generally proportional to the amount of water injected.

EXAMPLE 10

The system of Example 4 is equivalently reproduced except that the eluent stream exiting from the detector is not directed to waste but is instead directed back to the eluent reservoir to be reused for an extensive length of time in the laboratory of a DBNPA production plant. The eluent reservoir is sealed to prevent the absorption of water from the laboratory air into the eluent. The HPLC system is used to determine water in DBNPA formulations for production control purposes and the HPLC system continues to function for more than 1 month without maintenance despite the buildup of sample (including water) in the eluent. It is contemplated that in some systems using recycled eluent that an eluent drying means could be employed to control the buildup of water in the eluent, e.g., by placing a column filled with drying agent between the detector and the eluent reservoir. A drying column can also be used between the eluent pump and the injection valve.

This example shows the economy of operation using a recycled eluent and the long term ruggedness of the system routinely used in a chemical production plant.

What is claimed is:

1. A method for the determination of water by liquid chromatography comprising the steps of:
adding a predetermined volume of a sample containing a water component and another component to a flowing stream of a nonaqueous eluent;
eluting the sample through a separating medium effective to separate the water component from said another component so that the separated water component emerges from the separating medium in an effluent eluent stream; and
electrochemically detecting the separated water component in the effluent eluent stream from the separating medium in a manner effective to obtain a signal to noise ratio of greater than two.

2. The method of claim 1 wherein the detecting step is accomplished using a dielometry detector.

3. The method of claim 1 wherein the detecting step is accomplished using an electrical conductivity detector.

4. The method of claim 1 wherein the detecting step is accomplished using an oxidation/reduction detector.

5. The method of claim 1 wherein the detecting step is accomplished with a detector comprising electrodes and including the further step of placing an immobilized electrolyte between the electrodes of the detector, said electrolyte being in contact with said effluent eluent stream.

6. The method of claim 1 wherein the eluent contains less than about 100 parts per million water.

7. The method of claim 1 wherein the eluent contains less than about 300 parts per million water.

8. The method of claim 1 wherein the eluent contains less than about 5,000 parts per million water.

9. The method of claim 1, 2, 3, or 4 including the further step of adding an electrolyte to the effluent eluent stream before said detecting step, said electrolyte being effective to increase the signal to noise ratio of said detecting step.

10. The method of claim 9 wherein said electrolyte is an acid.

11. The method of claim 10 wherein said acid comprises a member of the group consisting of $H_2SO_4$, HCl or paratoluenesulfonic acid.

* * * * *